United States Patent [19]

Engeler

[11] 4,155,259

[45] May 22, 1979

[54] ULTRASONIC IMAGING SYSTEM

[75] Inventor: William E. Engeler, Scotia, N.Y.

[73] Assignee: General Electric Company, Schenectady, N.Y.

[21] Appl. No.: 908,907

[22] Filed: May 24, 1978

[51] Int. Cl.² ............................................ G01N 29/00
[52] U.S. Cl. ...................................... 73/626; 128/660; 340/5 MP
[58] Field of Search .................. 73/602, 620, 625, 626, 73/628; 340/1 R, 3 R, 5 R, 5 MP; 128/2 V, 2.052

[56] References Cited

U.S. PATENT DOCUMENTS

| | | | |
|---|---|---|---|
| 3,918,024 | 11/1975 | Macovski | 340/5 MP |
| 4,005,382 | 1/1977 | Beaver | 73/626 |
| 4,012,952 | 3/1977 | Dory | 73/626 |
| 4,058,003 | 11/1977 | Macovski | 340/1 R |
| 4,079,352 | 3/1978 | Burckhardt et al. | 340/1 R |

*Primary Examiner*—Stephen A. Kreitman
*Attorney, Agent, or Firm*—Julius J. Zaskalicky; Joseph T. Cohen; Marvin Snyder

[57] ABSTRACT

A B-scan ultrasound probe imaging system including an array of annular transducers is described in which dynamic focussing is provided by coherent demodulation of the echo signals generated in the transducers. As the range from which echoes are being received increases, coherent demodulation is maintained. The system provides improved lateral resolution over a greatly extended useful range.

11 Claims, 23 Drawing Figures

ULTRASONIC IMAGING SYSTEM

The present invention relates to apparatus for ultrasonic imaging and more particularly to such apparatus utilizing an array of annular transducers to provide a B-scan type of ultrasonic probe.

This application is related to U.S. patent application Ser. No. 908,908 filed concurrently herewith and assigned to the assignee of the present invention.

Prior art B-scan ultrasonic probe imaging system for imaging object points, such as soft tissue features of the human body, comprise in general a single disc-shaped transducer functioning as both a transmitting and a receiving transducer. The radiating surface of the disc transducer is often flat but may constitute the inner surface of a portion of a sphere, the center of which is the focal point of the transducer. The transducer is excited by an electrical pulse to generate a burst of ultrasound consisting of several cycles of oscillation at the resonant frequency of the transducer, which emanates in a beam into the space or object region surrounding the transducer. The burst of ultrasound on impinging on tissue or object points produce echoes which are reflected and received by the transducer and generates therein an echo signal which is also typically of several cycles duration. The echo signal is displayed on a suitable time base and thus a representation of the object points from which the echo was reflected as a function of range is obtained. The transducer may be moved along the surface of the body along a line to scan different portions of the body lying essentially in the plane of the beam and the line. With the display device suitably synchronized with the movement of the transducer along the body, a B scan display may be provided.

The z-axis resolution, that is, the resolution along a normal to the radiating surface of the disc transducer is a function of the duration of the excitation pulses applied to the transducer, or expressed in other words, the number of cycles of oscillations included in a transmitted burst. The lateral resolution of the transducer, that is, the resolution in a direction perpendicular to the normal to the transducer is dependent on the width of the beam at a range from which echoes are being received. A beam of large diameter provides lateral resolution of one value, and conversely a beam of small diameter at the range under consideration provides lateral resolution of another value representing better resolution. Lateral resolution refers to the minimum separation at which two targets or object points can be distinguished in a plane normal to the central or z-axis of the transducer. Not only is it important to provide good resolution at a particular range, but it is highly desirable to provide good lateral resolution continuously from a range near the transducer to a range which extends a considerable distance out from the transducer, i.e. in both the near field and the far field. Typically, in applications of such transducers in providing B-scans of the human body a range from 5 to 20 centimeters is highly desirable. By providing a slight curvature to the radiating surface of the transducer a beam may be provided which is essentially of uniform cross-section perpendicular to the z-axis in the near field. While such a transducer provides lateral resolution which is substantially uniform in the near field, the lateral resolution there is still rather poor as the cross-section of beam is relatively large. Utilization of a transducer of higher frequency would permit the reduction of the cross-section of the beam and hence would improve the lateral resolution, but at a sacrifice of depth of penetration into the body tissue. Improved lateral resolution may be obtained at a particular range by increasing the diameter of the disc transducer and providing a radius to the radiating surface which focuses on the selected range. The cross-section of the beam at this range is small. The cross-section of the beam progressively increases at ranges greater than this range and also progressively increases at ranges less than this range. Thus, while lateral resolution is improved at the desired range, the range over which the lateral resolution is improved is limited.

To further improve the lateral resolution it has been proposed that a probe be provided comprising an array of annular transducers of successively larger radii concentrically arranged about a central axis of the array. The radiating surface of the array of annular transducers may constitute the inner surface of a segment of a sphere, the center of which is the focal point of the array. The transducers of the array would be excited simultaneously by electrical pulses to generate a burst of ultrasound consisting of several cycles of oscillation at the resonant frequency of the transducers. Object points spaced along the central axis at a range less than the focal point of the array produce echoes which arrive at the various annular transducers at different times due to the difference in time of propagation of echoes from such object points to the annular transducers. High resolution is provided at the range of such an object point by appropriately delaying the echo signals generated by an echo from such a point so that they occur at the same time and may be coherently summed. If the time delays are made variable, coherent summation may be provided for object points which are near to the center of the array to object points which are at considerable distances from the center of the array, simply by appropriately varying the time delay for the signals generated in the transducers as a function of time or range. It has been proposed to use charge coupled delay lines in which delay can be made a function of frequency to provide such variable delays. The use of such delay lines in such a way, however, presents difficulties particularly with respect to the production of artifacts which considerably deteriorate any coherently summed signal.

The present invention is directed to overcoming limitations and problems, such as described above, in prior art ultrasonic B-scan probe imaging apparatus.

A principal object of the present invention is to provide a real time B-scan ultrasonic probe type imaging system in which improved lateral resolution is obtained over a greatly extended useful range.

In carrying out the invention in one illustrative embodiment thereof there is provided a means for producing and directing a burst of ultrasound of a predetermined frequency into an object region. An array of transducers which includes a plurality of annular transducers of successively larger radii concentrically arranged about a central axis of the array is provided to receive echoes of ultrasound produced by the burst of ultrasound impinging on object points lying on the central axis of the array. Each echo from a respective object point produces in the transducers a respective set of echo signals, one echo signal in each transducer. The time of occurrence of each of the echo signals is dependent on the distance between a respective transducer and the respective object point. A plurality of first demodulating signals of substantially the same frequency as the aforementioned predetermined frequency and of different relative phases is provided, the phase of each of the first demodulating signals in relation to the phase of a respective echo signal is set to substantially the same value. A means is provided for demodulating the echo signals obtained from the transducers and includes mixing each of the echo signals with a respective one of the first demodulating signals to obtain a respective first demodulated signal. A means is provided for weighting and summing the first demodulated signals to obtain a first sum signal.

The novel features which are believed to be characteristic of the present invention are set forth with particularity in the appended claims. The invention itself, both as to its organization and method of operation, together with further objects and advantages thereof may best be understood by reference to the following description taken in connection with the accompanying drawings wherein:

FIGS. 4A through 4H are also diagrams of amplitude vs. time of voltage signals occurring at various points in the sub-system of FIG. 2 associated with the Q channels thereof.

Figure 1A:
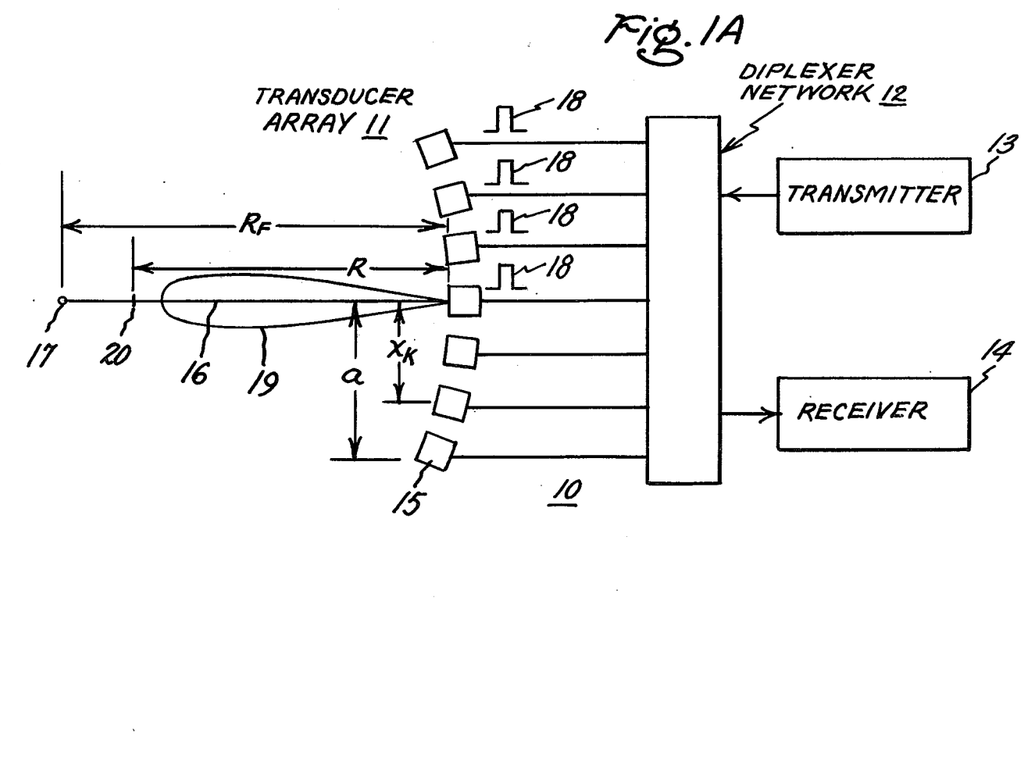
FIG. 1A is a block diagram illustrating the operation of an ultrasound imaging system.
Figure 1B:
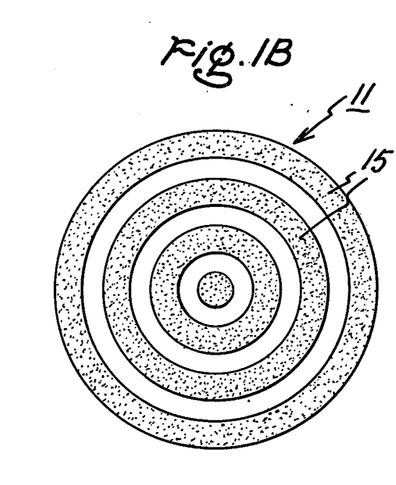
FIG. 1B is a plan view of array of annular transducers of the system of FIG. 1A.

Reference is made to FIG. 1A which shows a block diagram of the general organization of an ultrasonic imaging system 10 in accordance with one embodiment of the present invention. The ultrasonic imaging system 10 includes a transducer array 11, a diplexer network 12, a transmitter 13 and a receiver 14. In this embodiment of the invention the transducer array 11, as more completely shown in FIG. 1b, is an array of annular transducers 15 of successively larger radii concentrically arranged about a central axis 16 of the array. The resonant frequency of each of the transducers of the array is substantially the same. The radiating surface of the transducers constitutes the inner surface of a segment of a spherical surface, the center of which is the focal point 17. The transducer array functions as both a transmitting array and a receiving array. The transmitter 13 develops electrical pulses 18 which are simultaneously applied through the diplexer network 12 to the transducers 15 to develop a burst of ultrasound. The burst of ultrasound consisting of several cycles of oscillation at the resonant frequency of the transducers emanates into the object region adjacent the array. The variation of the intensity or amplitude of the burst of ultrasound about the mid-point of the array is referred to as the beam of the array. The beam 19 of array 11 is shown as having an axis coincident with the central axis 16 of the array 11. Echoes produced by the burst of ultrasound impinging on the focal point 17 are sensed at the same time by the transducers 15. The echo signals produced in transducers 15 by the echoes from the focal point 17 are passed through the diplexer network 12 to the receiver 14 where they are summed to produce a sharply focussed sum signal. The signals developed at the output of the receiver are suitably displayed on an oscilloscope to provide a display of the object region which may be a portion of a human body, for example. Echoes produced by the burst of ultrasound impinging on targets on the central axis 16 spaced from the focal point, such as object point 20, are sensed by the transducers 15 at different times due to the differences in the propagation paths from the object point 20 to the transducers. The greater the spacing of the object point 20 from the focal point 17, the greater would be the differences in the propagation paths and hence the greater would be the time delays. The summation of such echo signals produce a less sharply focussed sum signal. For example, if the propagation path difference between the center transducer and the outer transducer corresponds to one-half the wavelength of the ultrasound burst, the echo signals from these transducers would cancel. Also echo signals from the other transducers would partially cancel each other and thus a considerably reduced sum signal would result. Thus, for object points having central transducer to edge range differences greater than one-half the wavelength of ultrasound considerably reduced output is obtained limiting usefulness of the apparatus to regions in the vicinity of the focal point. The relative time delay for each transducer is given by the equation:

$$T_k = \frac{a^2}{2c} \left[ \frac{1}{R} - \frac{1}{R_f} \right] \left[ 1 - \left( \frac{x_k}{a} \right)^2 \right], \quad (1)$$

where $T_k$ = the time delay associated with the echo signal generated in the $k^{th}$ transducer produced by an echo from object point 20 in relation to the echo signal produced by an echo from focal point 17.

a = the half-aperture distance of the array,

R = the distance or range to the object point 20,

R = the distance or range to the focal point 17, c = the velocity of ultrasound in the object region, and $x_k$ = the distance from the center of the array to the $k^{th}$ transducer.

Figure 2:
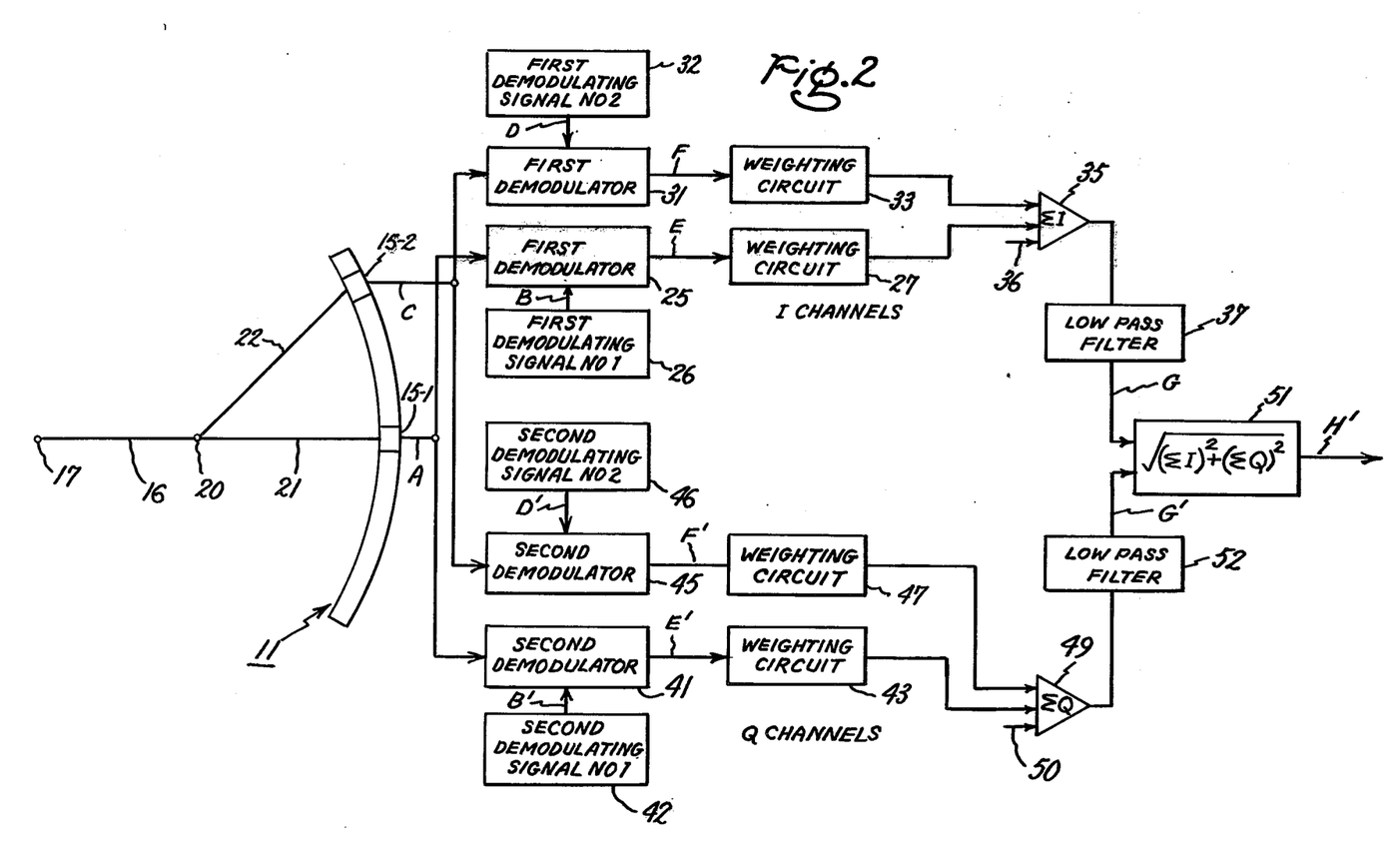
FIG. 2 is a functional block diagram of a sub-system of an ultrasound imaging system useful in explaining the principles of the present invention.

Reference is now made to FIG. 2, which shows a functional block diagram of apparatus in an ultrasound imaging system for processing echo signals in accordance with an embodiment of the present invention. The apparatus includes an array 11 of annular transducers 15 of successively larger radii concentrically arranged about a central axis 16 of the array. The resonant frequency of each of the transducers of the array is substantially the same. The radiating surface of the transducers constitutes the inner surface of a segment of a spherical surface, the center of which is the focal point 17. Point 20 represents an object point on the central axis 16 of the array. A burst of several cycles of ultrasound produced by the array impinges upon the object point 20 and generates an echo. The burst produced by a plurality of transducers of the array may be considered to originate at the center of the array. The echo is received at various transducers of the array at different times depending upon the distances between the object point 20 and the transducers of the array. Such an echo produces a set of echo signals in the transducers elements, one in each transducer. The processing of echo signals generated in transducers 15-1 and 15-2 will be particularly described. It will be understood that the echo signals generated in the other transducers are similarly processed. Transducer 15-1 is located at the center of the array and transducer 15-2 is located about the center of the array. Line 21 represents the propagation path of the echo reflected from object point 20 to the center of transducer 15-1. Line 22 represents the propagation path of the echo reflected from object point 20 to transducer 15-2.

The echo signal generated in the transducer 15-1 is referred to as echo signal No. 1 and the echo signal generated in transducer 15-2 is referred to as echo signals generated in each of the other transducers of the array are processed in a respective signal processing channel, referred to as an I channel. In each of the I channels the functions of demodulation and weighting are performed. Each of echo signals No. 1 and 2 as well as the other echo signals generated in the other transducers of the array are also processed in a respective Q signal processing channel in which the functions of demodulation and weighting are also performed. The demodulating signal utilized in each of the Q channels is set to be in phase quadrature relationship with respect to the demodulating signal utilized in the demodulation process in a respective I channel. The signals in the I channels are summed to obtain a first sum signal and the signals in the Q channels are also summed to obtain a second sum signal. The first sum signal and the second sum signal are filtered. From the filtered first sum signal and the filtered second sum signal a resultant signal is developed representing the reflection from the object point 20.

Figures 3A, 3B, 3C, 3D, 3E, 3F:
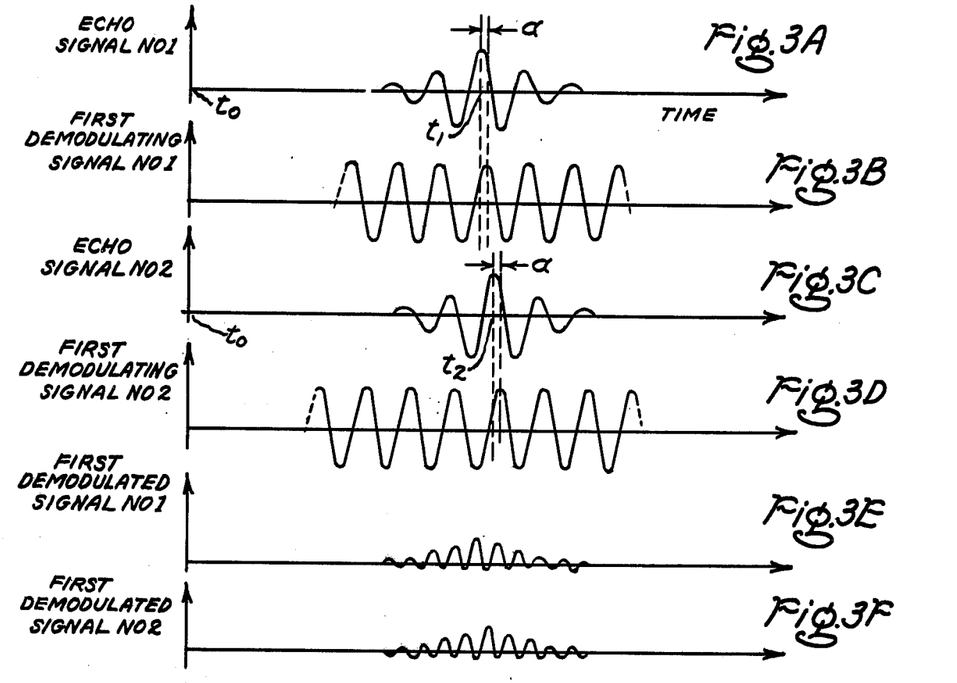
FIGS. 3A through 3G are diagrams of amplitude vs. time of voltage signals occurring at various points in the sub-system of FIG. 2 associated with the I channels thereof. The point of occurrence of a signal of FIGS. 3A through 3G in the block diagram of FIG. 2 is identified in FIG. 2 by the letter of the figure designation of the signal.

Reference is now made additionally to FIGS. 3A–3G. The point of occurrence of a signal of FIGS. 3A–3G in the block diagram of FIG. 2 is identified in FIG. 2 by the letter of the figure designation of the signal. Echo signal No. 1 generated in transducer 15-1 is shown in FIG. 3A. The peak of echo signal No. 1 occurs at a time $t_1$ after the time of occurrence $t_0$ of the peak of the burst of ultrasound launched by the array. The time of occurrence $t_1$ of the peak of the echo signal No. 1 depends on the distance 21 between the object point 20 and the transducer 15-1. Echo signal No. 1 is applied to a first demodulator 25 to which source 26 also applies first demodulating signal No. 1, shown in FIG. 3B. First demodulating signal No. 1 and the other first demodulating signals to be referred to in this description have a fundamental frequency substantially equal to the resonant frequency of the transducers. While the waveform of the first demodulating signals is shown as sinusoidal other waveforms, such as square waveforms, may be used. First demodulating signal No. 1 is shown lagging in phase with respect to echo signal No. 1 by phase displacement $\alpha$. The first demodulator 25 provides at its output first demodulated signal No. 1 shown in FIG. 3E, representing the product of echo signal No. 1 and first demodulating signal No. 1. First demodulated signal No. 1 is applied to weighting circuit 27 which provides a predetermined gain or attenuation factor to the first embodiment signal No. 1 so that it can be appropriately summed with similarly processed I channel signals from other transducers of the array in summation amplifier 35.

Echo signal No. 2 generated in transducer 15-2 is shown in FIG. 3C. The peak of echo signal No. 2 is shown as occurring at a time $t_2$ after the time of occurrence $t_0$ of the peak of the burst of ultrasound launched by the array. The time of occurrence $t_2$ of the peak of the echo signal No. 2 depends upon the distance 22 between the object point 20 and the transducer 15-2. Echo signal No. 2 is applied to demodulator 31 to which source 32 applies first demodulating signal No. 2, shown in FIG. 3D. First demodulating signal No. 2 is set lagging in phase with respect to echo signal No. 2 by phase displacement $\alpha$, the same phase displacement utilized in connection with echo signal No. 1 and first demodulating signal No. 1. To meet this requirement the phase of first demodulating signal No. 2 is changed with respect to the phase of first demodulating signal No. 1 by an amount dependent on the difference in propagation distances 21 and 22. First demodulated signal No. 2, shown in FIG. 3F, appears at the output of the first demodulator 31, representing the product of echo signal No. 2 and first demodulating signal No. 2. After weighting by the weighting circuit 33, the first demodulated signal No. 2 is applied to summation amplifier 35.

Figure 3G:
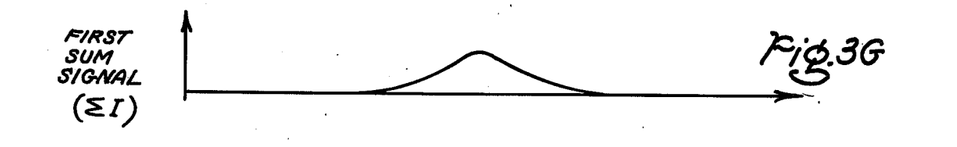

First demodulated signal No. 1 and first demodulated signal No. 2 are summed in sum amplifier 35 and filtered in low pass filter 37 to provide a first sum signal, shown in FIG. 3G. Echo signals generated in each of the other transducers of the array are processed in a similar manner and summed as collectively indicated by arrow 36 to provide at the output of sum amplifier 35 and after filtering by low pass filter 37 a large amplitude signal $\Sigma I$ representing contributions of all of the echo signals generated in the transducers of the array to the first sum signal.

Figures 4A, 4B:
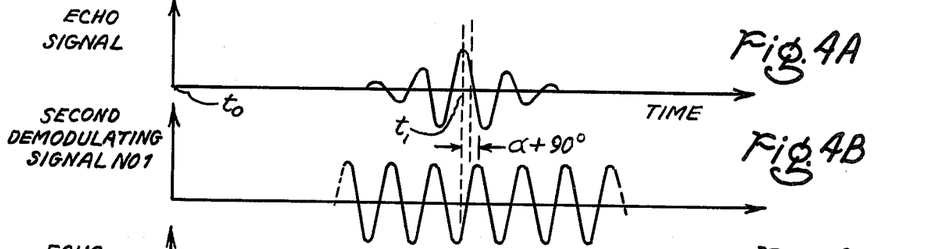
Figures 4C, 4D:
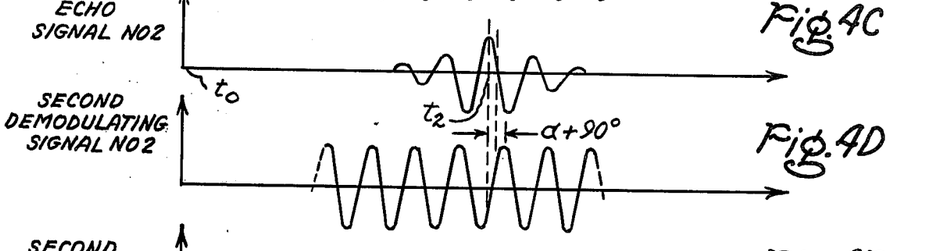
Figures 4E, 4F:
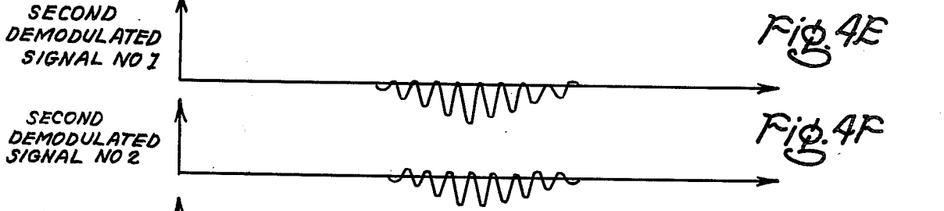

Reference is now made additionally to FIGS. 4A—4H. The point of occurrence of a signal of FIGS. 4A–4H in the block diagram of FIG. 2 is identified in FIG. 2 the letter primed of the figure designation of the signal. Echo signal No. 1 generated in transducer 15-1 is shown in FIG. 4A. As mentioned in connection with FIG. 3A, the peak of echo signal No. 1 occurs at a time $t_1$ after the time of occurrence $t_0$ of the peak of the burst of ultrasound launched by the array. The time of occurrence $t_1$ of the peak of the echo signal No. 1 depends on the distance 21 between the object point 20 and the transducer 15-1. Echo signal No. 1 is applied to a second demodulator 41 to which source 42 also applies second demodulating signal No. 1 shown in FIG. 4B. Second demodulated signal No. 1 and the other second demodulating signals to be referred to in this description have a fundamental frequency substantially equal to the resonant frequency of the transducers. While the waveform of the second demodulating signals is shown as sinusoidal, other waveforms such as square waveforms may be used. Second demodulating signal No. 1 is set to be lagging by 90 degrees the phase of first demodulating signal No. 1 or $\alpha+90$ degrees lagging in phase the phase of echo signal No. 1. The second demodulator 41 provides at its output second demodulated signal No. 1 shown in FIG. 4E, representing the product of echo signal No. 1 and second demodulating signal No. 1. Second demodulated signal No. 1 is applied to weighting circuit 43 which provides a predetermined gain or attenuation factor of the second demodulated signal No. 1 so that it can be appropriately summed with similarly processed Q channel signals from other transducers of the array in summation amplifier 49.

Echo signal No. 2 generated in transducer 15-2 is shown in FIG. 4C. As mentioned in connection with FIG. 3C, the peak of the echo signal No. 2 is shown as occurring at a time $t_2$ after the time of occurrence $t_0$ of the peak of the burst of ultrasound launched by the array. The time of occurrence $t_2$ of the peak of the echo signal No. 2 depends upon the distance 22 between the object point 20 and the transducer 15-2. Echo signal No. 2 is applied to second demodulator 45 to which source 46 also applies second demodulating signal No. 2, shown in FIG. 4D. Second demodulating signal No. 2 is set to be lagging by 90 degrees of the phase of the first demodulating signal No. 2 or $\alpha+90$ degrees lagging in phase the phase of echo signal No. 2. Second demodulated signal No. 2, shown in FIG. 4F, appears at the output of the second demodulator 45, representing the product of echo signal No. 2 and second demodulating signal No. 2. Second demodulated signal No. 2 is applied to weighting circuit 47 which provides a predetermined gain or attenuation factor to the second demodulated signal No. 2 so that it can be appropriately summed with similarly processed Q channel signals from other transducers of the array in summation amplifier 49.

Figure 4G:
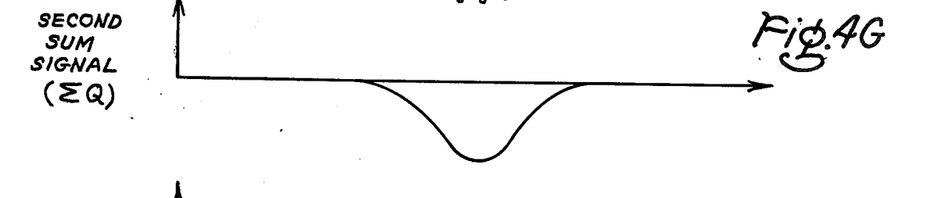
Figure 4H:
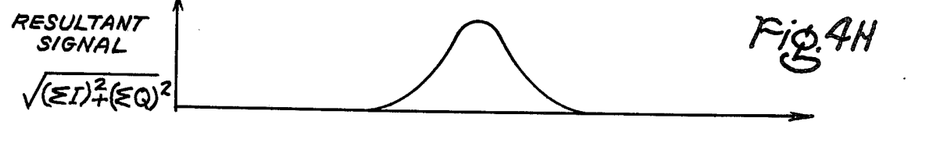
FIG. 4H is a diagram of the resultant signal formed from the signals of FIGS. 3G and 4G. The point of occurrence of a signals of FIGS. 4A through 4H in the block diagram of FIG. 2 is identified in FIG. 2 by the letter primed of the figure designation of the signal.

Second demodulated signal No. 1 and second demodulated signal No. 2 are summed in sum amplifier 49 and filtered in low pass filter 52 to provide a second sum signal, shown in FIG. 4G. Echo signals generated in each of the other transducers of the array are processed in a similar manner and summed, as collectively indicated by arrow 50, to provide at the output of the sum amplifier 49 and after filtering by low pass filter 52 a large amplitude signal $\Sigma Q$ representing contributions of all of the echo signals generated in the transducers of the array to the second sum signal.

The first sum signal at the output of low pass filter 37 and the second sum signal from the output of low pass filter 52 are applied to a circuit 51 for deriving a resultant signal which is a monotonic function of the sum of the square of the first sum signal and the square of the second sum signal. More particularly the circuit provides a resultant signal which is proportional to the square root of the sum of the square of the first sum signal and the square of the second sum signal. The circuit 51 provides a resultant signal the amplitude of which is independent of the setting of the phase of each of the first demodulating signals in respect to a respective one of the echo signals, and of course independent of the setting of each of the second demodulating signals in respect to a respective one of the echo signals as each second demodulating signal is set in phase quadrature relationship to a respective one of the first demodulating signals. This result will be readily understood from a consideration of the following example. As the first demodulating signal No. 1 of FIG. 3B lags the phase of the echo signal No. 1 of FIG. 3A by $\alpha$ degrees, the peak amplitude of the first demodulated signal No. 1 of FIG. 3E is equal to cosine $\alpha$ times the maximum value that the first demodulated signal No. 1 may have corresponding to the situation in which the first demodulating signal No. 1 of FIG. 3B is in phase with the echo signal No. 1 of FIG. 3A. As the second demodulating signal No. 1 of FIG. 4B lags the phase of the echo signal No. 1 by $(\alpha+90)$ degrees, the amplitude of the second demodulated signal No. 1 of FIG. 4E may be represented by the cosine $(\alpha+90)$ times the maximum possible amplitude that the second demodulated signal No. 1 may have corresponding to the condition in which the second demodulating signal No. 1 is in phase with the echo signal No. 1. To obtain the maximum value of the first demodulated signal No. 1 it is simply necessary to take the square root of the sum of the square of the first demodulated signal No. 1 and the second demodulated signal No. 1. Noting that $\sqrt{\cos^2\alpha+\cos^2(\alpha+90)}$ is independent of $\alpha$ and is equal to one, it is apparent that the maximum value of the first demodulated signal is proportional to the peak of echo signal No. 1. As each of the other echo signals are processed in the same way it is clear that the result illustrated in the above example is valid for the first sum signal $\Sigma I$ and for the second sum signal $\Sigma Q$. In FIG. 3A through 3D the phase displacement or angle $\Sigma$ is shown as 60 degrees. Also in FIGS. 4A through 4D the angle $\alpha$ is shown as 60 degrees. Thus, by utilizing a pair of I and Q channels for the processing of each echo signal a resultant signal is obtained which is independent of the angle $\alpha$. However, in order to prevent cancellation when the sum signals are formed, the angle $\alpha$ for each first demodulating signal and a respective echo signal must be substantially the same. This result is accomplished by setting the phase of each of the first demodulating signals with respect to one another so that the relationship of each first demodulating signal with respect to a respective echo signal is substantially the same. The phase setting of each first demodulating signal is dependent on the propagation distance from the object point 20 to a respective transducer. As each second demodulating signal is set in quadrature lagging relationship with respect to a respective first demodulating signal, the proper phase relationship for each of the second demodulating signals is automatically obtained.

For proper operation of the sub-system of FIG. 2 the phase of each first demodulating signal in relation to the phase of a respective echo signal should be substantially the same for all pairs of signals. Of course, the phasing of the second demodulating signals are fixed by the phasing of the first demodulating signals. An object point at a different range would require different relative phasing of the first demodulating signals and also, of course, of the second demodulating signals to obtain the ideal response at the output of the sum amplifiers 35 and 49. For small increments in range from the range of object point 20 the relative phase requirements of the first demodulating signals and of the second demodulating signals do not change sufficiently to cause a significant departure in performance from the performance that would be obtained were the ideal relative phases utilized. However, at some point differing in range from that of object point 20 the changing relationships of the propagation times to the transducers causes performance to become marginal, and it is necessary to provide a new set of relative phase relationships for the first and second demodulating signals to obtain approximately ideal performance. This new set of relative phase relationships would be valid for a certain range span beyond which another set of phase relationships would be provided. In general, as the ultrasound burst moves deeper into the object region, the object point focussed on is caused to track the burst by sequentially adjusting the phase relationships of the demodulating signals in discrete steps or continuously. The manner in which the phases of the first and second demodulating signals may be reset to accommodate the different requirements for relative phase settings with range will be described in connection with the functional block diagram of FIG. 5.

Successive echoes received from successive object points successively more distant, i.e. at greater ranges, from the array produce successive sets of electrical signals in the transducers of the array 11. Successive sets of first demodulating signals and second demodulating signals would be provided with the proper relative phase relationships as explained above. The resultant signal appearing at the output of circuit 51 would include elements corresponding to echoes received from the successive object points. A plurality of bursts of ultrasound may be applied to the array to produce a plurality of echo signals and a plurality of resultant signals at the output of circuit 50. The resultant signals may then be suitably displayed in various scan modes on a display device to provide a visual indication of the tissue structure of the body within the field of view. The manner in which the relative phases of the first demodulating signals and the second demodulating signals are preset during the period of reception of echoes from an object region and the manner in which the relative phases of the first demodulating signals and the second demodulating signals are changed with range to maintain coherent demodulation will be described in connection with FIG. 5.

Figure 5:
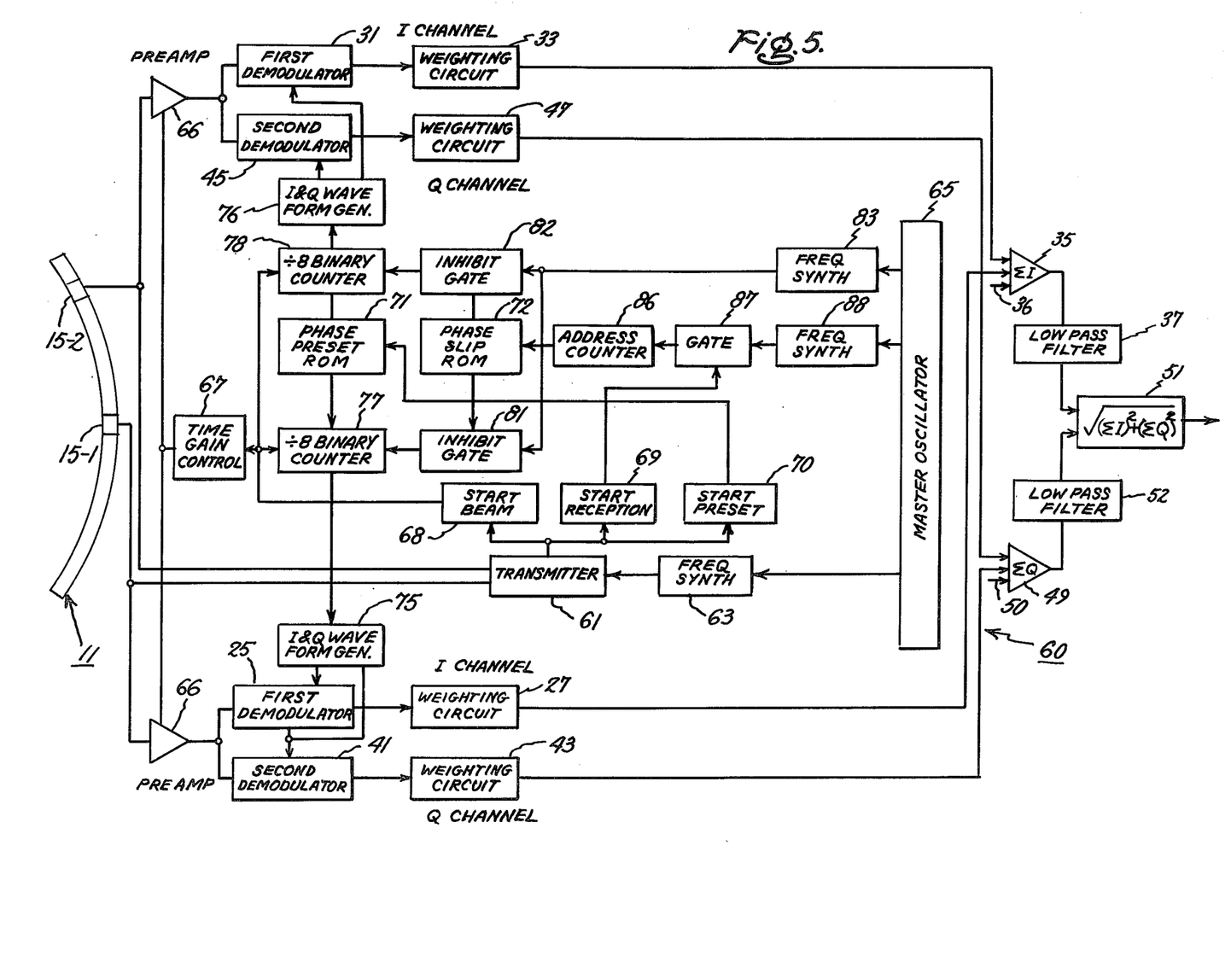
FIG. 5 is a functional block diagram of the ultrasonic imaging system embodying the present invention.

Reference is now made to FIG. 5 which shows a functional block diagram of an ultrasound imaging system 60 incorporating one embodiment of the invention disclosed and described in connection with FIG. 2. The elements of FIG. 5 identical to the elements of FIG. 2 are identically designated. Transmitter 61 provides simultaneous pulses of proper duration to the transducers of the linear array 11 to form a transmitting beam which is oriented along the central axis of the array. Frequencies for the operation of the transmitter 61 are supplied by frequency synthesizer 63 connected to master oscillator 65.

A plurality of preamplifiers 66 are provided, each connected between a respective transducer and a respective pair of I and Q signal processing channels to provide echo signals of suitable amplitude for processing. A time gain control circuit 67 provides an output signal to each of the preamplifiers 66 to equalize the amplitudes of the echo signals developed in the various transducers of the array 11 as a function of range to facilitate the processing thereof. The time gain control circuit 67 is activated after each transmitted burst of sound by a start beam signal received from start beam circuit 68 and synchronized with the pulses from transmitter 61. The start beam signal is also utilized to initialize the divide-by-eight counters 77 and 78. A start preset circuit synchronized with pulses from transmitter 61 provides a start preset signal to a phase preset ROM (Read Only Memory) 72 in which is stored phase preset data for initiating pre-setting of the phases of the I and Q waveform generators of the system, as will be explained below. I and Q waveform generator 75 provides the outputs produced by first demodulating signal generator 26 and second demodulating signal generator 42 of FIG. 2. I and Q waveform generator 76 provides the outputs provided by the first demodulating signal generator 32 and second demodulating signal generator 46. A start reception circuit 69 synchronized with the pulses supplied by the transmitter 61 develops a start reception signal following the occurrence of a start beam signal which is utilized to control a phase slip sequence for the signal processing channels associated with the various transducers of the array, as will also be explained below in greater detail.

The manner in which the above-mentioned functions are implemented will now be described. First, consider the manner in which the relative phases of the first and second demodulating signals in the various channels is preset to provide coherent demodulation for a receiving beam having a particular number. The first and second demodulating signals for echo signal from transducer 15-1 are provided by I and Q waveform generator 75. The first and second demodulating signals for the echo signal from transducer 15-2 are provided by I and Q waveform generator 76. Each of the first and second demodulating signals in each of the channels can be preset to any one of eight positions displaced from one another by 45 degrees. The generator 75 is under the control of divide-by-eight binary counter 77. The generator 76 is under the control of divide-by-eight binary counter 78. Any one of eight possible phase positions of each of the divide-by-eight counters is obtained by presetting the divide-by-eight counter by a respective three-bit word. The three-bit words are obtained from the phase preset ROM 71. A plurality of three-bit words are stored in ROM 71, each word representing the phase setting of a respective I and Q waveform generator. Thus, on appearance of a start preset signal from a start preset circuit 70 activated by transmitter 61 after each transmitted burst of ultrasound, ROM 71 is accessed to provide the proper presetting of the divide-by-eight binary counters of all of the channels. On appearance of the start beam signal from start beam circuit 68, the divide-by-eight binary counters 77 and 78 are enabled. Pulses occurring at a frequency eight times greater than the frequency of the echo signals generated in the transducers are applied to each of the divide-by-eight binary counters 77 and 78 through respective ones of inhibit gates 81 and 82 from a frequency synthesizer 83 which derives its input from master oscillator 65. Thus, after a burst of ultrasound has been transmitted information is supplied from the phase preset ROM 71 to each of the eight-bit binary counters associated with a respective signal processing channel to develop first and second demodulating signals of the proper phase relationship in respect to the first and second demodulating signals in the other channels to enable coherent demodulation of the echo signals in an initial range zone of the object region. Since all channels receive the same clock pulses, any difference in phase preset counts present at the beginning of a scan will be maintained throughout the scan.

It was pointed out above that in order to provide the proper relative phasing of the first and second demodulating signals in the various signaling processing channels with respect to one another it is necessary to change the phase of each of the first and second demodulating signals with range to maintain this proper relative phasing. The manner in which phasing of the first and second demodulating signals of each channel changes with range is dependent on the position of the transducer in relation to the center of the array of transducers will now be described. The amount by which the phase of the first and second demodulating signals of a channel must be changed with range to maintain coherent demodulation of the echo signal can be readily ascertained from a consideration of equation 1. The time delay $T_k$ is a function of range R, the particular transducer element under consideration $x_k$. The relative time delay $T_k$ may be converted into a phase variable at the resonant frequency of the transducers by dividing this dependent variable by the period of a cycle at the resonant frequency of the transducers. Thus, the phase change required for a given transducer element $x_k$ varies inversely with range R, or time. The manner in which this relationship is utilized to provide phase slippage with range for each of the signal processing channels will now be explained. The slippage in phase of the first and second demodulating signals of a signal processing channel is provided by deleting or inhibiting a pulse from a sequence of pulses supplied to the divide-by-eight binary counters, such as counters 77 and 78, from the frequency synthesizer 83 through inhibit gates, such as inhibit gate 81 and 82. Each of the inhibit gates is supplied a sequence of bits from the phase slip ROM 72. Whenever there is a change from a bit to its complement, or vice versa, a pulse is inhibited by the inhibit gate from passing through to the divide-by-eight binary counter, thus, causing a slippage in phase of 45 degrees of the binary counter. The phase slip ROM 72 is provided with a sequence of words at sequential addresses. The number of bits in each word is equal to the number of channels in the system. Like numbered bits in successive words are provided in sequence to a corresponding inhibit gate in accordance with the sequential counting of the address counter 86. The address counter 86 is connected through a gate 87 to a frequency synthesizer 88 which is under the control of master oscillator 65. The frequency synthesizer 88 provides an output signal of a particular frequency corresponding to velocity of penetration of the beam into the object region. The gate 87 blocks the passage of the output signal from the frequency synthesizer 88 to the address counter 86 prior to the occurrence of a start reception signal from start reception circuit 69. On appearance of the start reception signal at gate 87, the output from frequency synthesizer 88 is applied to the address counter 86. The rate at which the address counter 86 runs through the addresses is dependent on the frequency provided by the frequency synthesizer 88.

The operation of the apparatus of FIG. 5 will now be described over a pulse-echo cycle or period of operation thereof. Just prior to the application of simultaneous excitation pulses to the transducers of the array 11 from transmitter 61 a start preset signal from start preset circuit 70 is applied to the phase preset ROM 71 and accesses data addressed thereby. The data is fed to the divide-by-eight binary counters 77 and 78 associated with each signal processing channels to preset the divide-by-eight binary counters to an initial count which corresponds to the phase relationship appropriate to the array geometry. This assures that the I and Q waveform generators 75 and 76 are properly phased with respect to one another to enable coherent demodulation of echo signals received by the transducers of the array from the near field of view of the array 11.

Shortly after the excitation pulses from the transmitter 61 develop the burst of ultrasound which emanates from the array 11, a start beam signal from start beam circuit 68 is generated and is applied to time gain control circuit 67 which controls the gain of the preamplifier 66 as a function of range to equalize the amplitudes of the received echo signals generated in the transducers of the array. The start beam signal also enables the divide-by-eight binary counters, such as counters 77 and 78, to initiate their count and thus enables the I and Q waveform generators, such as generators 75 and 76, to generate the I and Q waveforms for the various channels of the apparatus to coherently demodulate the various echo signals appearing in these channels. The echo signals are produced first by echoes from the object points in the near field of the array.

Shortly after the start beam signal, a start reception signal is developed by the start reception circuit 69 and is applied to gate 87 which is opened and enables the signal appearing at the output of frequency synthesizer 88 to be applied to the address counter 86 causing the latter to count at the rate determined by the frequency of the signal from frequency synthesizer 88. The address counter 86 cycles the addresses of the phase slip ROM 72 at a particular rate which causes the inhibit gates, such as gates 81 and 82, to drop pulses from the frequency synthesizer 83 and hence alter the phasing of the divide-by-eight binary counters. Slipping the phases of the divide-by-eight binary counters enables the phases of the I and Q waveforms of all of the signal processing channels to be maintained at relative values which maintain coherent demodulation of echo signals developed by echoes reflected from object points more distant from the array. The processed echo signals after weighting are summed in the summation amplifiers 35 and 49. The signals from the summation amplifiers 35 and 49 after filtering in low pass filters 37 and 52, respectively, are applied to the circuit 51 which develops an output which is proportional to the square root of the sum of the square of the summation signal $\Sigma I$ and the square of the summation signal $\Sigma Q$. The output of the circuit 51 is referred to as a video signal and has amplitude variations corresponding to echo intensity at various ranges as a function of time. This signal may be applied to various display devices, such as an oscilliscope, to display the amplitude of the signal as a function of time to provide a visual indication of the object points such as body tissue as a function of time or range. The array may be moved along the surface of the body along a line to scan different portions of the body line essentially in the plane of the beam and the line. With the display device suitably synchronized with the movement of the transducer along the body a TM or time-motion display may be provided. In such a mode of operation utilized of the I channel or Q channel signal processing circuits alone would provide a useful display.

Transducers 15 of array 11 may have any resonant frequency. Typically the resonant frequency of the transducers 15 may be between 2.0 to 5.0 megahertz. The frequency of the I and Q waveform generators 75 and 76 and hence the frequency of the divide-by-eight binary counters 77 and 78 would be substantially the same as the resonant frequency of the transducers 15. The frequency of the output of the frequency synthesizer 83 would be eight times the fundamental frequency of the divide-by-eight binary counters, and accordingly, for transducers of resonant frequency of 2.25 megahertz, would be 18 megahertz. Conveniently, the pulses provided by the transmitter could have a duration of time about two microseconds which would produce oscillations of several cycles in the transducers when excited thereby. The repetition rate of the transmitter pulses conveniently may be the order of 3 kilohertz. The frequency is related to the depth of penetration and reflection of ultrasound from object points in the object region into which the ultrasound is directed by the array. The frequency synthesizer 63 provides appropriate frequency information for the generation of pulses of such duration and repetition rate by the transmitter 61. The frequency of the output of the frequency synthesizer 88 utilized for phase slip operation lies in the range of the frequency of the frequency synthesizer 83. Preferably, this range should not include either the video band of frequencies or the region of frequencies close to the resonant frequency of the transducers. Master oscillator 65 provides frequencies which may be several times higher than the highest frequency utilized in the system to enable the frequencies developed by the various frequency synthesizers to have the proper values.

Conveniently the array 11 may comprise about 10 transducer elements each 0.95 millimeter wide and spaced on about 0.1 millimeter centers.

Figure 6A:
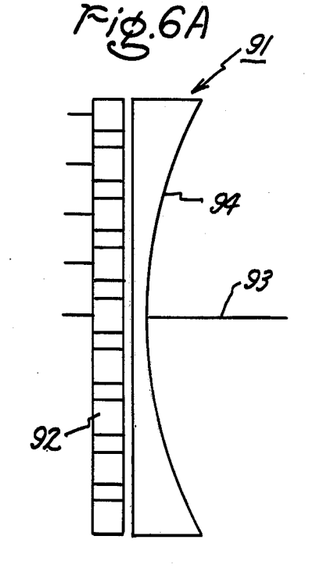
FIG. 6A is a plan view of an array of annular transducers provided with a fixed focus.
Figure 6B:
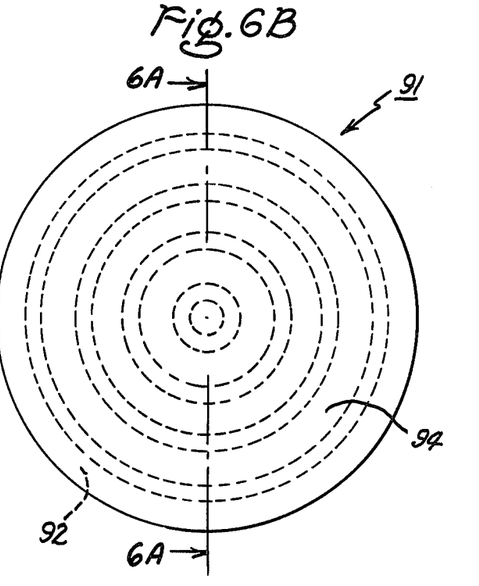
FIG. 6B is a sectional view of the array of FIG. 6A taken along section lines 6B—6B thereof.

Reference is now made to FIGS. 6A and 6B which shows another annular transducer array assembly 91 provided with a fixed focus which may be utilized in place of the transducer array 11 in the apparatus of FIGS. 1A, 2 and 5. The annular transducer array assembly 91 comprises annular transducers 92 of successively larger radii concentrically arranged about a central axis 93. The radiating surfaces of the annular transducers 92 lie in a plane normal to the central axis 93. An acoustic lens 94 is mounted in front of the annular transducers 92 and is made of a material, such as an appropriate plastic in which the velocity of sound is faster than the object region in connection with which the transducer is to be used, for example, body tissue. The surface of the lens 94 adjacent the radiating surface of the annular transducers 92 is planar and the opposite surface is curved so that isochronous path delays for sound are provided from a focal point lying on the central axis 93 to all of the elements 92 of the array.

Figure 7A:
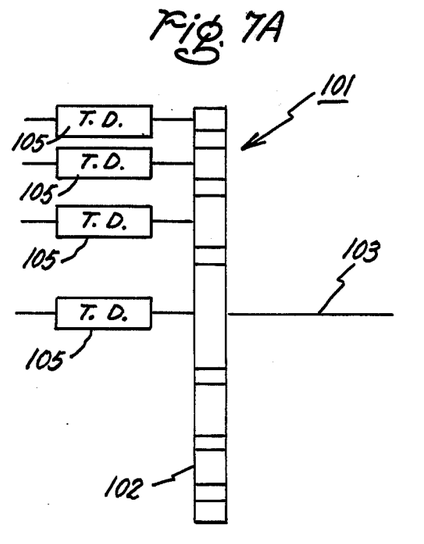
FIG. 7A is a plan view of another array of annular transducers provided with a fixed focus.
Figure 7B:
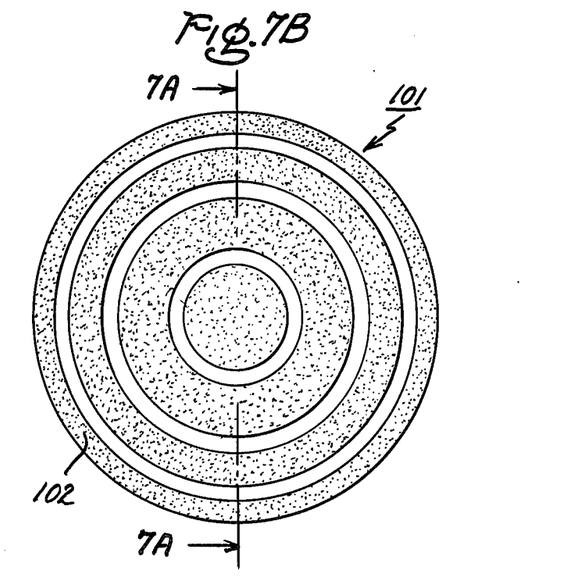
FIG. 7B is a sectional view of the array of FIG. 7A taken along sectional lines 7B—7B thereof.

Reference is now made to FIGS. 7A and 7B which shows still another transducer array assembly 101 suitable for use in the apparatus of FIGS. 1A, FIG. 2 and FIG. 5 in place of the transducer array 11. The transducer array assembly 101 comprises an array of annular transducers 102 of successively larger radii concentrically arranged about a central axis 103 of the assembly. The radiating surfaces of the transducers 102 lie in a plane perpendicular to the central axis 103. The transducers 102 are provided with a geometry and a spacing so that the radiating surfaces of each of the transducers is substantially the same. Such an organization provides efficient use of the signal processing channels with which the transducers are to be used. A fixed focus lying on the central axis 103 is provided by the connection of time delay circuits 105 to each of the transducers. The time delay provided in each of the time delay circuits 105 is such that the signals appearing at the output of the time delay circuits in response to an echo from the focal point occur at the same time.

While the invention has been described in connection with imaging of tissue structure within the human body for medical diagnostic purposes, it is apparent that the system may be used for other purposes, such as for fault detection in castings.

While the invention has been described in specific embodiments it will be appreciated that modifications, such as those described above, may be made by those skilled in the art and it is intended by the appended claims to cover all such modifications and changes as fall within the true spirit and scope of the invention.

What I claim as new and desire to secure by Letters Patent of the United States is:

1. An ultrasound imaging system comprising
   means for producing and directing a burst of ultrasound of a predetermined frequency into an object region,
   an array including a plurality of annular transducers of successively larger radii concentrically arranged about a central axis of the array, said array receiving an echo of ultrasound produced by said burst of ultrasound impinging on an object point lying on said central axis in said object region, said echo from said object point producing in said transducers a set of echo signals, the time of occurrence of each of said echo signals being dependent on the distance between a respective transducer and said object point,
   means for providing a plurality of first demodulating signals of substantially the same frequency as said predetermined frequency and of different relative phases, the phase of each of said first demodulating signals in relation to the phase of a respective echo signal being set to substantially the same value,
   means for demodulating the echo signals obtained from said transducers including means for mixing each of said echo signals with a respective one of said first demodulating signals to obtain a respective first demodulated signal,
   means for weighting and summing the first demodulated signals to obtain a first sum signal.

2. The system of claim 1 in which successive echoes are received from successive object points lying along said central axis in said object region producing successive sets of echo signals in said transducers,
   means for providing successive pluralities of first demodulating signals of the same frequency as said predetermined frequency and of different relative phases, each plurality corresponding to a respective set of successive echo signals, the phase relationship of each of said first demodulating signals of a plurality in relation to the phase of a respective echo signal of a corresponding set being set to substantially the same value,
   means for demodulating each set of echo signals obtained from said transducers to obtain a respective plurality of first demodulated signals including means for mixing each echo signal of a set with a respective one of said first demodulating signals of a corresponding plurality to obtain a first demodulated signal of a corresponding plurality,
   means for weighting and summing the first demodulated signals of each plurality to obtain a respective first sum signal.

3. The system of claim 2 in which corresponding first demodulating signals of successive pluralities of first demodulating signals are continuously changed in phase to provide the required phase relationship of said same value with respective to the corresponding echo signals of successive sets of echo signals.

4. The system of claim 1 including
   a means for providing a plurality of second demodulating signals of substantially the same frequency as said predetermined frequency, each second demodulating signal being in phase quadrature to a respective one of said first demodulating signals, a means for demodulating the echo signals obtained from said transducers including means for mixing each of said echo signals with a respective one of said second demodulating signals to obtain a respective second demodulated signal, means for weighting and summing the second demodulated signals to obtain a second sum signal, means for forming a resultant signal which is a substantially monotonic function of the sum of the square of said first sum signal and the square of said second sum signal.

5. The system of claim 2 including second means for providing successive pluralities of second demodulating signals of the same frequency as said predetermined frequency, each plurality of said second demodulating signals corresponding to a respective plurality of said first demodulating signals, each second demodulating signal of a plurality being in phase quadrature to a respective first demodulating signal of a corresponding plurality, second means for demodulating each set of echo signals obtained from said transducers to obtain a respective plurality of second demodulated signals including means for mixing each echo signal of a set with a respective one of said second demodulating signals of a corresponding plurality to obtain a respective second demodulated signal of a corresponding plurality.

means for weighting and summing the second demodulated signals of each plurality to obtain a respective second sum signal, means for forming a plurality of resultant signals each a substantially monotonic function of a respective sum of the square of a respective first sum signal and the square of a respective second sum signal.

6. The system of claim 5 in which corresponding first demodulating signals of successive pluralities of first demodulating signals are continuously changed in phase to provide the required phase relationship of said same value with respect to the corresponding echo signals of successive sets of echo signals, and in which corresponding second demodulating signals of successive pluralities of second demodulating signals are continuously changed in phase to provide the required phase quadrature relationship to corresponding first demodulating signals of successive pluralities of first demodulating signals.

7. The system of claim 1 including focussing means for providing a fixed focal point on the central axis of said array whereby first demodulated signals formed from echo signals produced by an echo from said focal point occur at the same time.

8. The system of claim 1 in which said focussing means includes means for delaying each of said echo signals produced by an echo from said object point in negative relationship to the difference in distance between said focal point and a respective one of said transducers.

9. The system of claim 1 in which said focussing means includes arranging said transducers so that they are equally distant from said focal point whereby equal time delays are provided for sound propagating from said focal point to all of the transducers of the array.

10. The system of claim 1 in which said focussing means includes arranging said transducers in a plane and providing adjacent thereto a converging acoustic lens made of a material in which the velocity of sound is faster than the speed of sound in said object region so that equal time delays are provided for sound propagating from said focal point to all of the transducers of the array.

11. The system of claim 1 in which the radiating surfaces of said annular transducer lie in a plane and have areas which are substantially equal.

* * * * *